(12) United States Patent
Sedillo (10) Patent No.: US 11,951,205 B2
(45) Date of Patent: Apr. 9, 2024

(54) PRODUCT OF AND METHOD FOR MAKING CHEMICAL FREE HUMAN HAIR SHAKERS

(71) Applicants: Richard Applegate, Coral Springs, FL (US); Karen Applegate, Coral Springs, FL (US)

(72) Inventor: Leanne Sedillo, Boca Raton, FL (US)

(73) Assignees: Richard Applegate, Coral Springs, FL (US); Karen Applegate, Coral Springs, FL (US)

( * ) Notice: Subject to any disclaimer, the term of this patent is extended or adjusted under 35 U.S.C. 154(b) by 606 days.

(21) Appl. No.: 17/154,302

(22) Filed: Jan. 21, 2021

(65) Prior Publication Data

US 2021/0220257 A1 Jul. 22, 2021

Related U.S. Application Data

(60) Provisional application No. 62/963,628, filed on Jan. 21, 2020.

(51) Int. Cl.
*A61K 8/98* (2006.01)
*A45D 40/00* (2006.01)
*A61K 8/891* (2006.01)

(52) U.S. Cl.
CPC .......... *A61K 8/985* (2013.01); *A45D 40/0075* (2013.01); *A61K 8/891* (2013.01); *A45D 2200/207* (2013.01); *A61K 2800/5424* (2013.01); *A61K 2800/82* (2013.01); *A61K 2800/87* (2013.01)

(58) Field of Classification Search
CPC ........ A61K 2800/87; A61K 2800/5424; A61K 2800/82; A61K 8/891
USPC ........................................................ 141/18
See application file for complete search history.

(56) References Cited

U.S. PATENT DOCUMENTS

2016/0309821 A1* 10/2016 Knight ................... A61K 8/985
2017/0311667 A1* 11/2017 Passariello ............. B65D 1/023

* cited by examiner

*Primary Examiner* — Jason K Niesz (57) ABSTRACT

A natural human shaker hair is offered to be efficiently applied to the balding spots and thinning areas of a user's scalp. The shaker hair comprises 100% natural human hairs and does not include any chemicals and/or man-made materials. The shaker hair is statically charged with negative electricity to not only allow easy application to the affected areas, but also cling to the user's scalp and existing hair. Thus, the shaker hair creates root lift and substantial kickstand support to the existing long hair of the user, and helps the user with desired styling. Further, an innovative method of making the all-natural human shaker hair is provided. The method prepares the shaker hair by cutting natural human hairs into hair granules and charging the hair granules with a charging machine. The resulting shaker hair charged with statically negative charge is placed into hair shakers and ready for use.

6 Claims, 8 Drawing Sheets

(A) Preparing hair granules by cutting or shattering natural human hairs into small lengths (B) Placing the prepared hair granules into a hair container (C) Attaching the hair container to a charging machine (D) Starting the charging machine at a room temperature of 10 °C to 30 °C to statically and negatively charge the hair granules in the hair container (E) Filling at least one shaker with the statically and negatively charged hair granules in the hair container

PRODUCT OF AND METHOD FOR MAKING CHEMICAL FREE HUMAN HAIR SHAKERS

The current application claims a priority to the U.S. Provisional Patent application Ser. No. 62/963,628 filed on Jan. 21, 2020.

FIELD OF THE INVENTION

The present invention relates generally to cosmetics. More specifically, the present invention relates to a cosmetic shaker hair that is pure human hair without any chemicals. The present invention is used to conceal and/or obscure a user's balding spots and thicken thinning hair by efficiently sprinkling thereon the present invention, which is charged with negative static electrical charge. Additionally, the present invention provides a method of making the chemical free human hair shakers.

BACKGROUND OF THE INVENTION

According to American Academy of Dermatology, an average adult loses about 50-100 hairs every day. Most people who have a healthy hair growth cycle normally grow new hairs as they lose old ones. However, this is not always the case for people who suffer from severe or even permanent hair loss. Hair loss, or alopecia, is a concern for men, women, and children. Every year in America, about 35 million men and 21 million women suffer from hair loss. Hair loss in men and women can be absolutely devastating to self-image and emotional well-being.

Hair loss can be caused by a variety of factors including stress and anxiety, hormone change and chemical imbalance, scalp infection, illness, medication, low iron, aging, vitamin deficiency, and certain hairstyle and treatment. For example, aggressive hairstyling such as over brushing or pulling hair tight in up-do can results in thinning hair and/or hair loss.

Among many hair loss treatment methods, a hair loss concealer, provides the most easy and convenient way to instantly obscure a user's balding spots and thinning areas while does not disrupt daily hair styling, thus improving the overall look and feel of hair, and making the hair loss concealer the convenient solution for a desired occasion or event. The existing hair loss concealer products are in the forms of powder, spray, and fragment. These products are easy to apply, cost effective, designed for both men and women, easy to wash out, various color styles, and do not restrict or compromise the growth of the user's natural hair. However, many hair loss concealers use fragments made of non-natural hair and comprise chemicals, color paint, additives, etc. These hair loss concealers may use cause itchiness and even damage to the user's scalp. Other problems and drawbacks include unpleasant odor, leaving flakes in the hair, staining clothing, not effective for users with severe hair loss, being messy to use, making the user feel heavy on head, hard to apply, applicator (such as a pump) being faulty, inconsistent quality, etc.

Therefore, it is an object of the present invention to provide a solution to the aforementioned problems and drawbacks of many existing hair loss concealers. The present invention offers the user an effective and natural human hair to efficiently apply to the balding spots and thinning areas of the user's scalp. Further, the present invention provides an innovative method of making the chemical free, natural human hair shakers.

SUMMARY OF THE INVENTION

The present invention provides an effective and natural human shaker hair to be efficiently applied to the balding spots and thinning areas of a user's scalp. The shaker hair comprises 100% natural human hair with original colors and does not include any chemicals, additives, color paints, or fragments. The shaker hair of the present invention is cut from human hair and statically charged with negative electricity to allow the shaker hair to not only be easily applied to the affected areas, but also cling to the user's scalp and existing hair. Thus, the shaker hair, in the form of short human hairs, creates root lift and substantial kickstand support to the long hair of the user, and helps the user with desired styling.

Further, an innovative and efficient method of making the chemical free, natural human shaker hair is also provided. The method prepares the shaker hair by cutting natural human hairs into hair granules of various small lengths and places the resulting short hair segments to a hair container. The hair container is then attached to a charging machine such as an ultrasonic static generation machine for electrical charging. During the charging process, the short hair segments of the shaker hair gain electrons and become statically and negatively charged. Subsequently, the user removes the shaker hairs from the hair container and pours the charged shaker hairs into hair shakers. Finally, the user seals the shakers with the caps and the present invention is ready for use.

DETAIL DESCRIPTIONS OF THE INVENTION

All illustrations of the drawings are for the purpose of describing selected versions of the present invention and are not intended to limit the scope of the present invention.

The present invention is a shaker hair that offers an effective and natural human hair to be efficiently applied to the balding spots and thinning areas of a user's scalp. The shaker hair of the present invention does not include any chemicals, additives, color paints, or fragments other than human hair. Specifically, the shaker hair of the present invention is statically charged with negative electricity to allow the shaker hair to not only be easily applied the affected areas, but also cling to the user's scalp and hair. Thus, the present invention, in the form of short human hairs, creates root lift and substantial kickstand support to the existing long hair of the user, and helps the user with desired styling.

Figure 1:
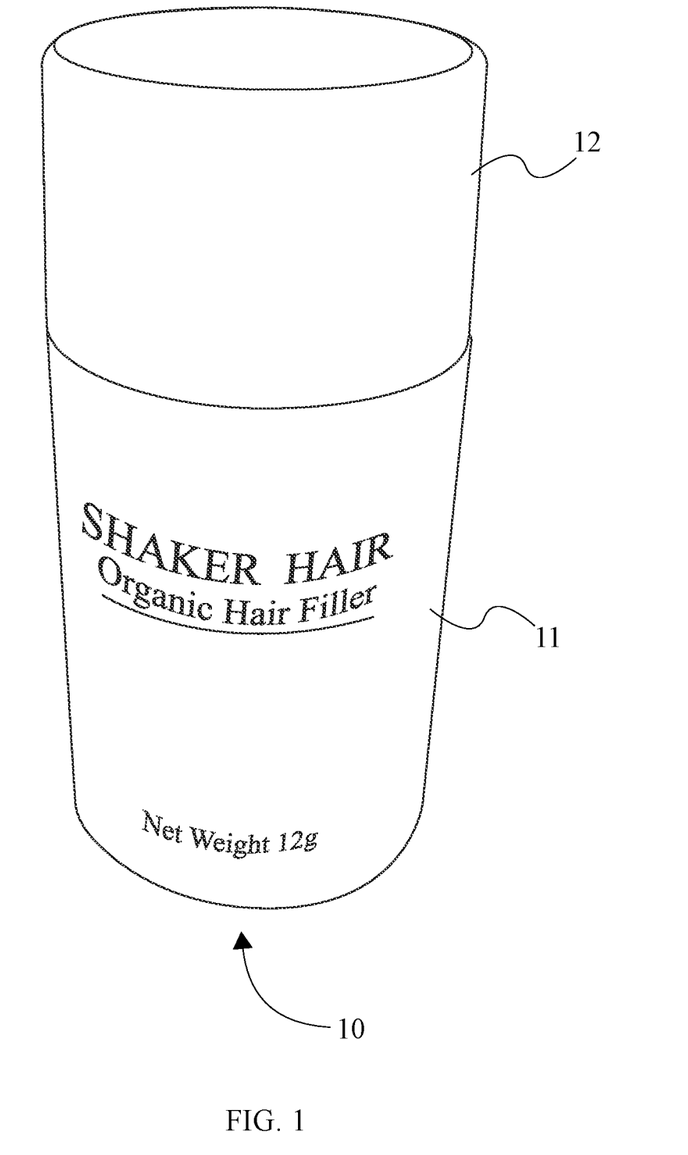
FIG. 1 is a photographic front view of one embodiment of a hair shaker of the present invention.
Figure 2:
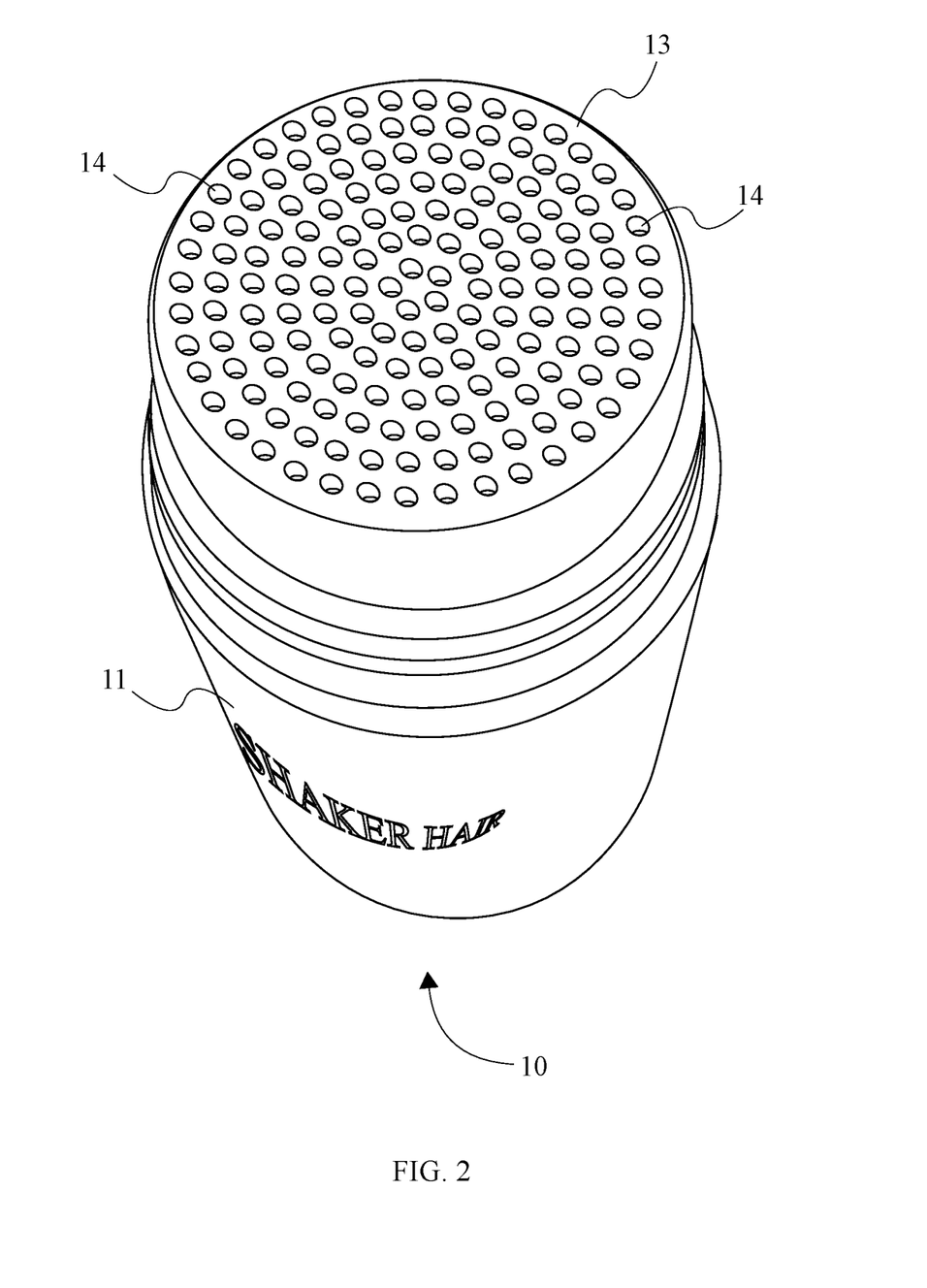
FIG. 2 is a photographic top view of the hair shaker of the present invention, wherein the cover of the hair shaker is removed.
Figure 3:
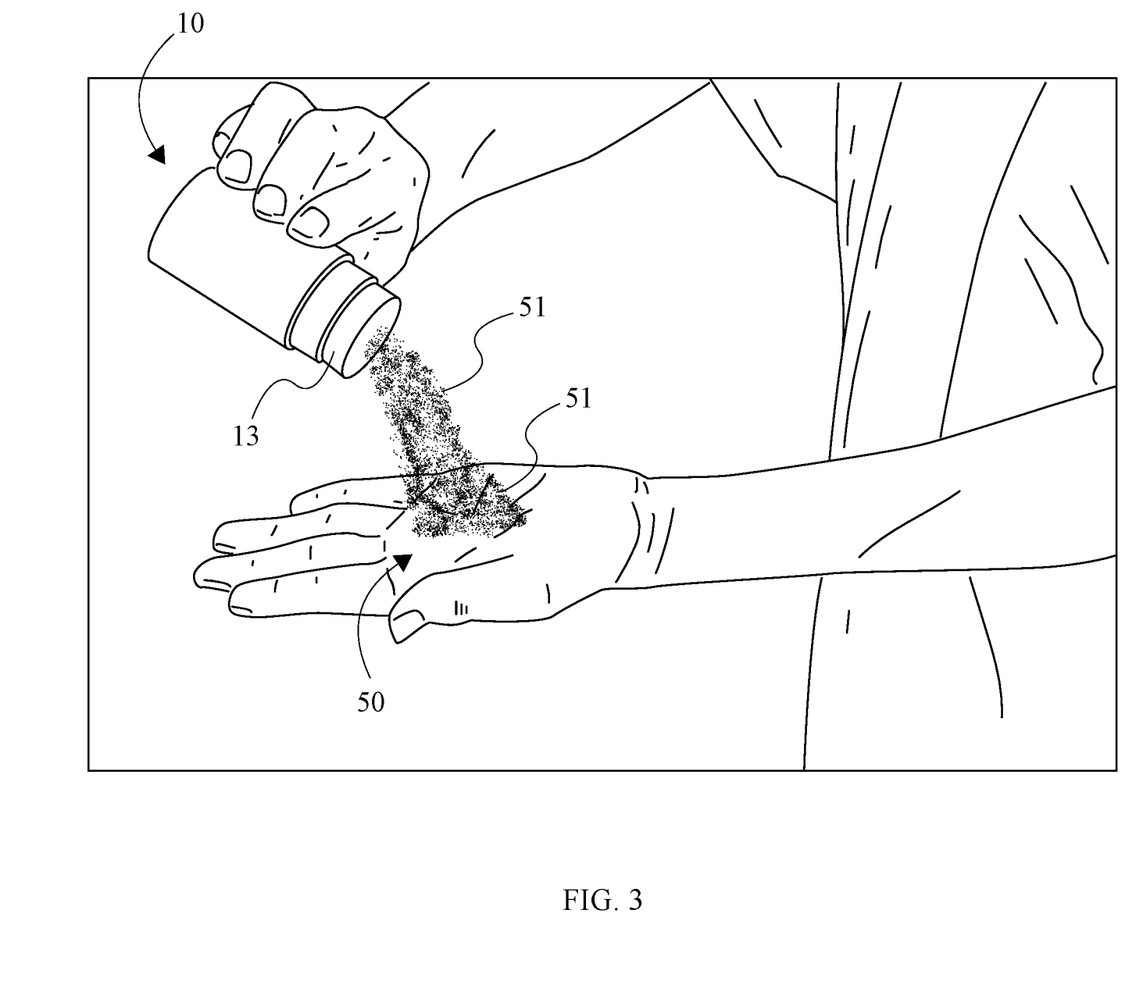
FIG. 3 is a photographic front view of one embodiment of the hair shaker of the present invention, wherein the shaker hair is being sprinkled onto a user's hand.

As can be seen in FIG. 1 to FIG. 3, the present invention comprises a hair shaker for providing natural human hair without any chemicals and non-natural materials. The hair shaker of the present invention comprises a shaker 10 and shaker hair 50. The shaker 10 is used to contain the charged shaker hair 50 and provides convenient and efficient application of the shaker hair segments onto the user's scalp. More specifically, the shaker 10 comprises a body 11, a cover 12, and a cap 13. The body 11 of the shaker 10 includes, but is not limited to, a cylindrical bottle, an oval bottle, a box-shaped container, or any other suitable shape or container. In the preferred embodiment of the present invention, the shaker 10 may comprise a plastic container. Other materials including, but not limited to, metal, glass, etc., may be used. Additionally, the body 11 of the shaker 10 comprises an opening 15. The cap 13 of the shaker 10 is terminally and removably attached to the body 11 covering the opening 15 of the body 11. More specifically, the cap 13 includes, but is not limited to, a thread, or a snap, or any other suitable means to be used so that the cap 13 can engage and hermetically seal the body 11 of the shaker 10. Additionally, the cap 13 comprises a plurality of holes 14, as can be seen in FIG. 2. The plurality of holes 14 is used to sprinkle the shaker hair 50 to the user's scalp for efficient and convenient application of the present invention. Further, the cap 13 can be mounted to the body 11 of the shaker 10 by conventional fastening mechanism including, but not limited to, threads, snaps, compression fitting, etc. The cover 12 is removably and terminally attached to the cap 13 covering the cap 13. Additionally, the cover 12 is positioned on and completely enclosing the cap 12, as can be seen in FIG. 1 to FIG. 3.

Figure 4:
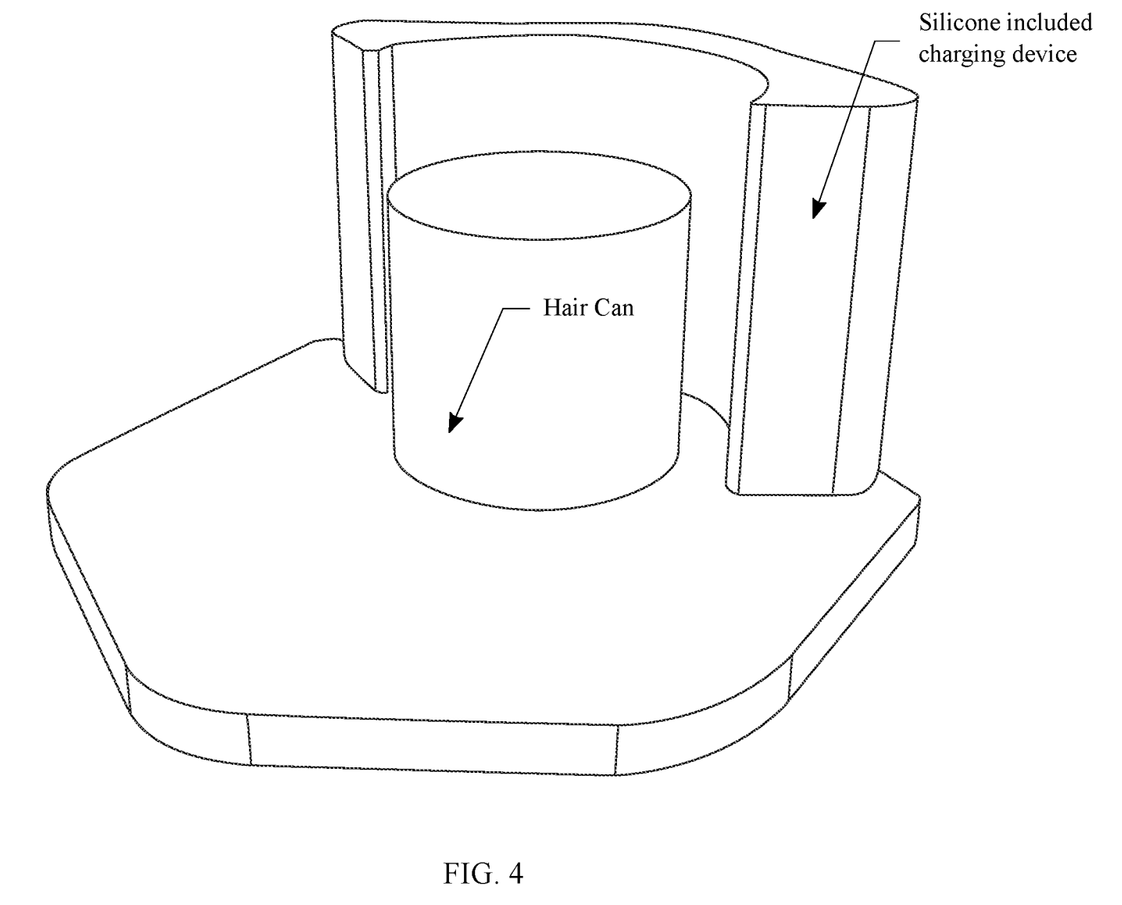
FIG. 4 is a photographic view of the charging machine used to statically charge shaker hair of the present invention.
Figure 5:
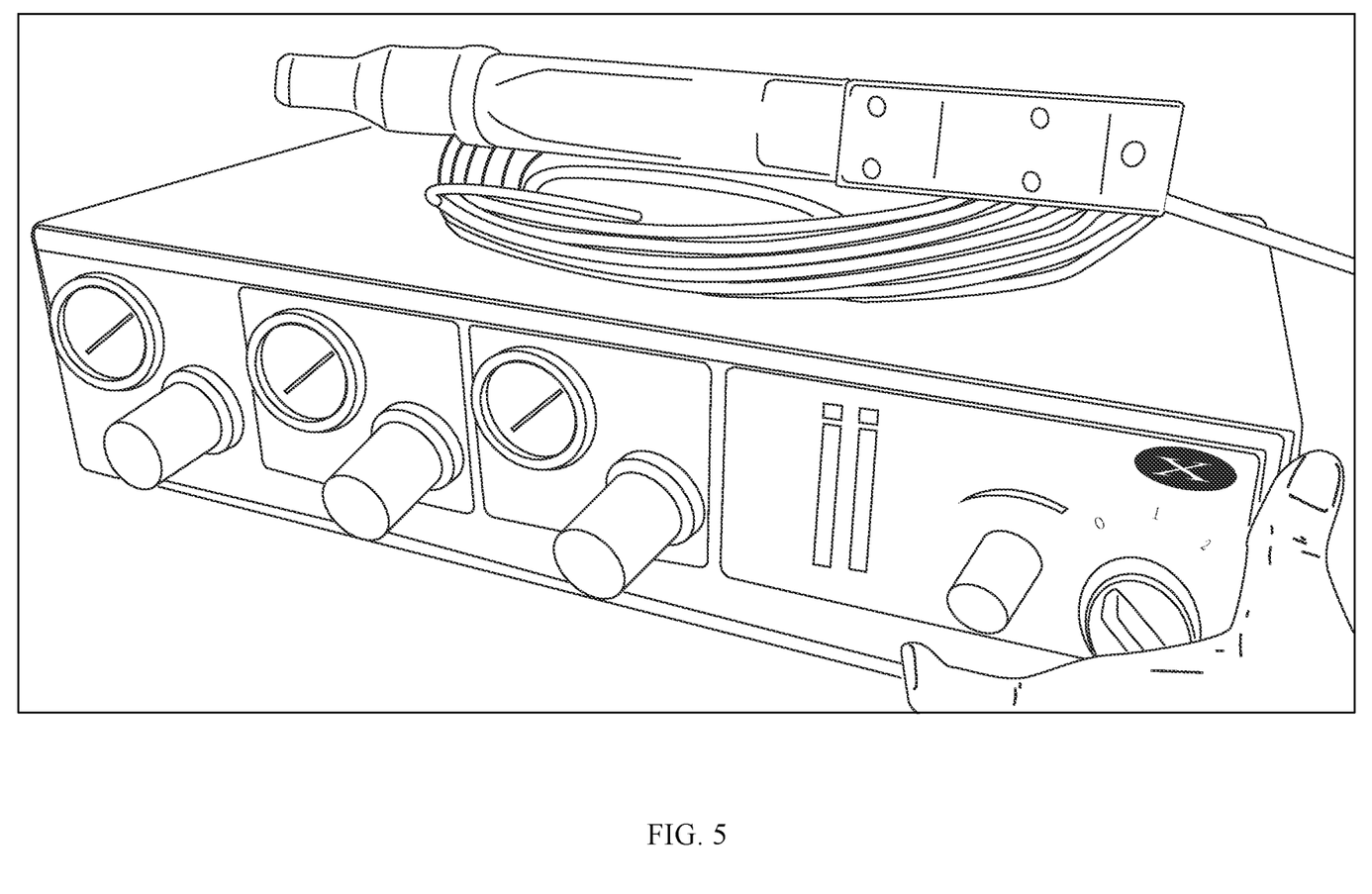
FIG. 5 is a front perspective view of the charging machine of the present invention.

As can be seen in FIG. 3, the shaker hair 50 of the present invention comprise a plurality of hair granules 51. The plurality of hair granules 51 is charged with negatively static electricity with static electricity using a charging machine, including, but not limited to, an ultrasonic static generation machine, as can be seen in FIG. 4 to FIG. 5. The plurality of hair granules 51 of the shaker hair 50 comprises short human hair segments in various lengths and in the form of, including, but not limited to, granules, hair shorts, short segments, etc. The plurality of hair granules 51 can have various natural colors, including, but not limited to, blond, black, brown, etc. No artificial colors such as dyes are used in the shaker hair 50. Further, the plurality of hair granules 51 of the shaker hair 50 is statically charged with negative electricity to provide the root lift and support to the existing long hair of the user when applied to the user's scalp. Additionally, the shaker hair 50 are removably positioned inside the body 11 of the shaker 10, as can be seen in FIG. 3.

Figure 6:
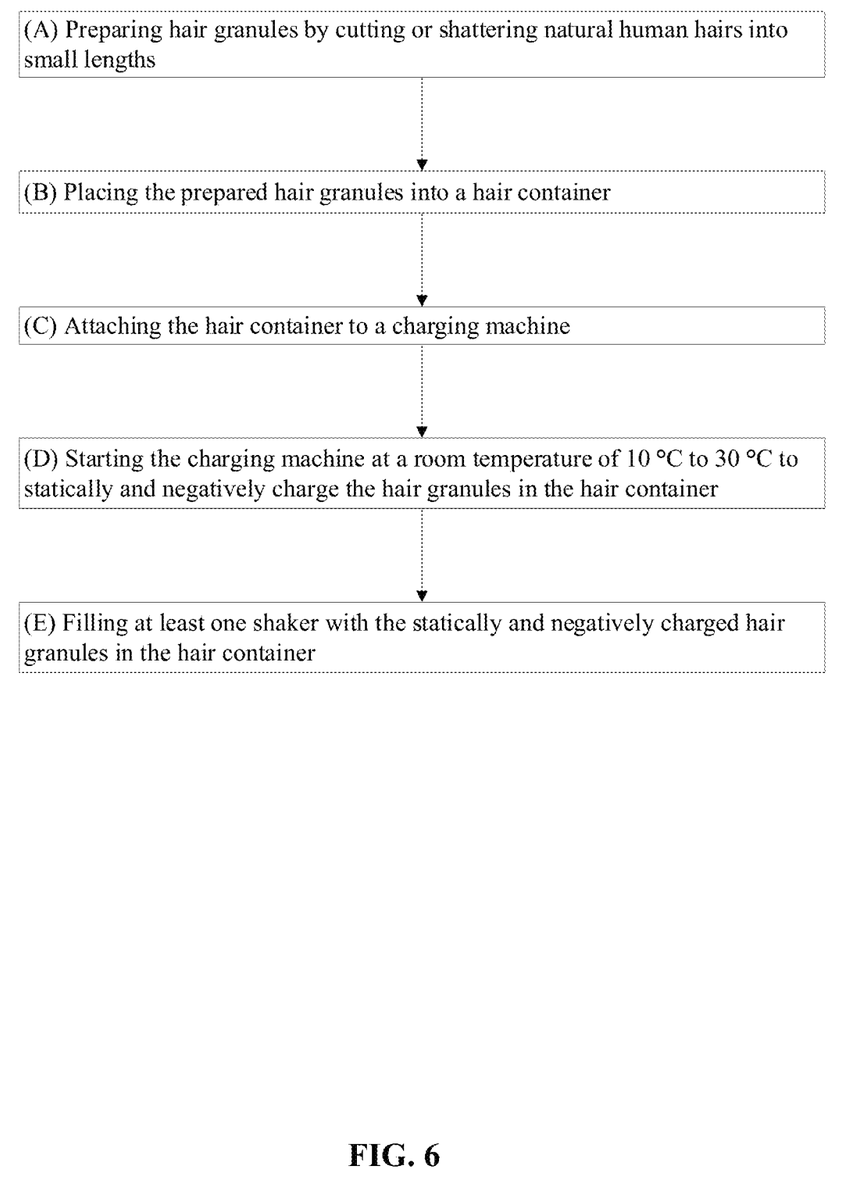
FIG. 6 is a flowchart of the overall process of making the shaker hair of the present invention.
Figure 7:
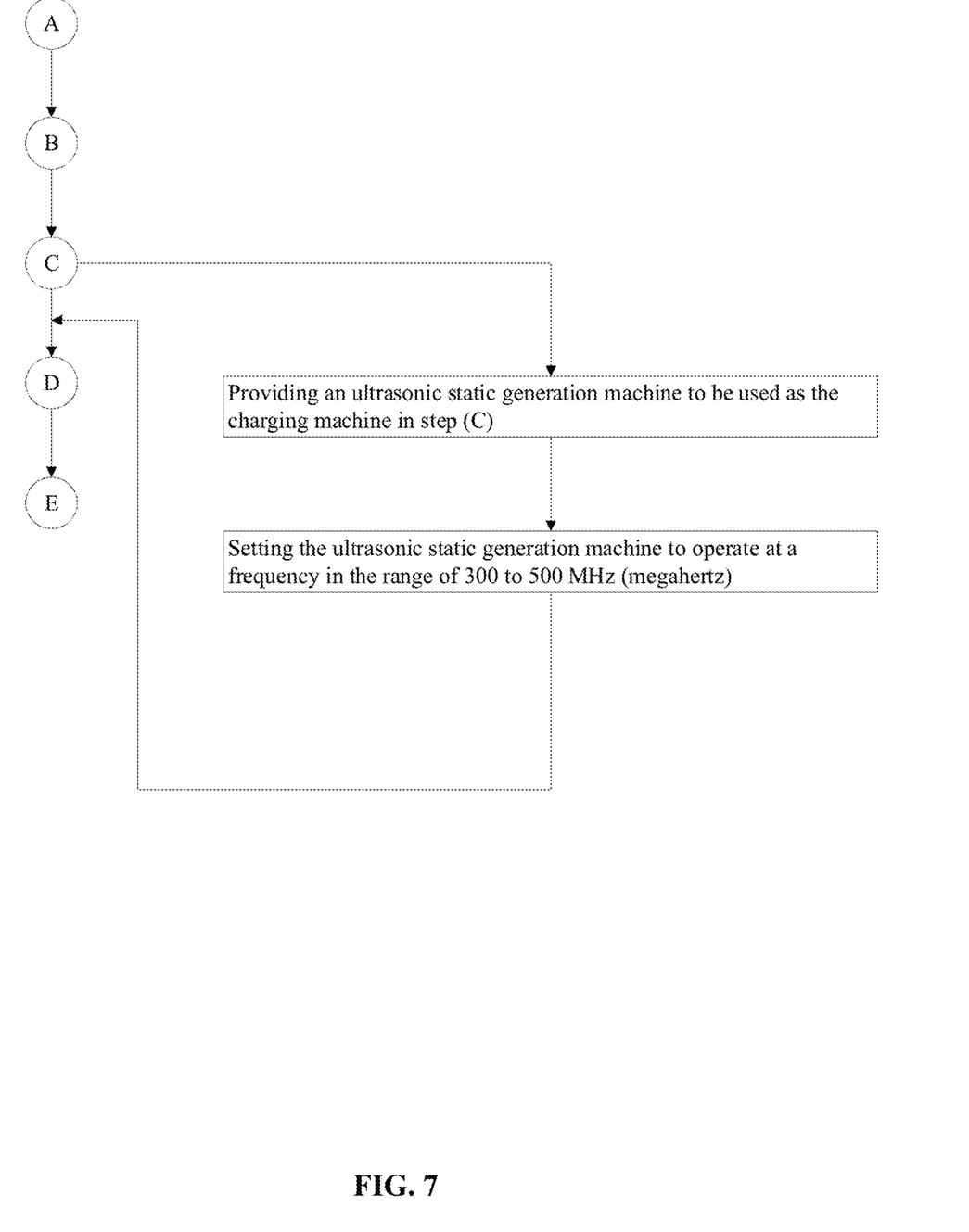
FIG. 7 is a flowchart of a sub-process of making the shaker hair of the present invention, wherein an ultrasonic static generation machine is provided.
Figure 8:
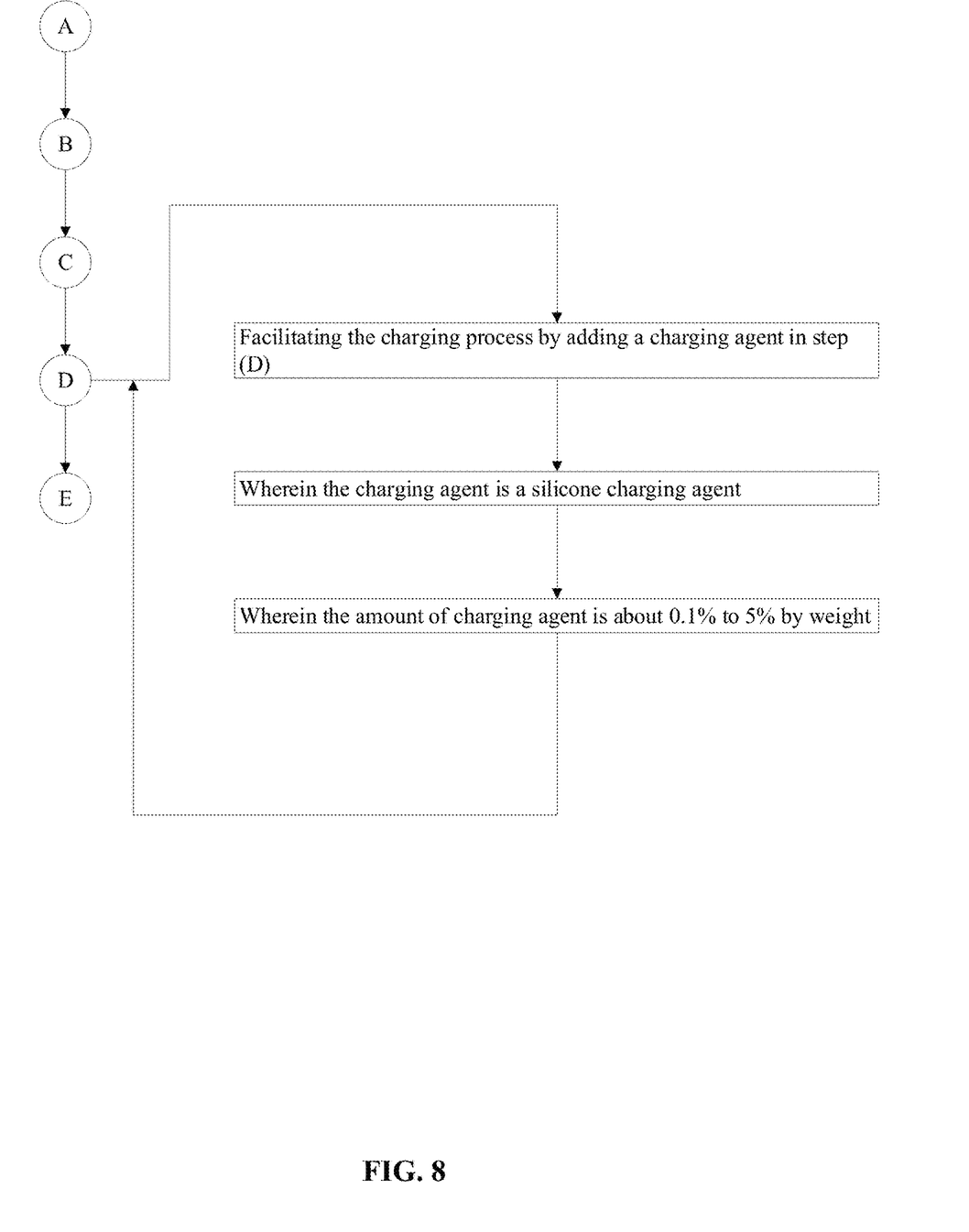
FIG. 8 is a flowchart of another sub-process of making the shaker hair of the present invention, wherein an optional charging agent is used in facilitating the charging process.

As can be seen in FIG. 6 to FIG. 8, the present invention provides a method of making natural human shaker hair. The overall process of the method of making the present invention starts with preparing hair granules by cutting or shattering natural human hairs into small lengths (Step A). Then the method places the prepared hair granules into a hair container (Step B) and attaches the hair container to a charging machine (Step C). Subsequently, the method starts the charging machine at a room temperature of 10° C. to 30° C. to statically and negatively charge the hair granules in the hair container (Step D). With the shaker hair being completely charged, the method fills at least one shaker with the statically and negatively charged hair granules in the hair container (Step E). Thus, the user can seal the hair shaker 10 with the cap 11 and the present invention is ready for use.

As can be seen in FIG. 7, the method provides an ultrasonic static generation machine to be used as the charging machine in Step C. Subsequently, the method sets the ultrasonic static generation machine to operate at a frequency in the range of 300 to 500 megahertz (MHz). During the charging process, the short hair segments of the shaker hair 50 gain electrons and become negatively charged. As can be seen in FIG. 8, in an alternative embodiment, the method of the present invention may facilitate the charging process by adding a charging agent in Step D. The optional charging agent used in this process may include, but is not limited to, a silicone charging agent. Additionally, the amount of charging agent includes, but is not limited to, about 0.1% to 5% by weight.

Although the invention has been explained in relation to its preferred embodiment, it is to be understood that many other possible modifications and variations can be made without departing from the spirit and scope of the invention as hereinafter claimed.

What is claimed is:

1. A method of making natural human shaker hair comprising:
   (A) preparing hair granules by cutting or shattering natural human hairs into small lengths;
   (B) placing the prepared hair granules into a hair container;
   (C) attaching the hair container to a charging machine
   (D) starting the charging machine at a room temperature of 10° C. to 30° C. to statically and negatively charge the hair granules in the hair container; and
   (E) filling at least one shaker with the statically and negatively charged hair granules in the hair container.

2. The method of making natural human shaker hair as claimed in claim 1 comprising the steps of:
   providing an ultrasonic static generation machine to be used as the charging machine in step (C).

3. The method of making natural human shaker hair as claimed in claim 2 comprising the steps of:
   setting the ultrasonic static generation machine to operate at a frequency in the range of 300 to 500 MHz (megahertz).

4. The method of making natural human shaker hair as claimed in claim 1 comprising the steps of:
   facilitating the charging process by adding a charging agent in step (D).

5. The method of making natural human shaker hair as claimed in claim 4 comprising the steps of:
   wherein the charging agent is a silicone charging agent.

6. The method of making natural human shaker hair as claimed in claim 5 comprising the steps of:
   wherein the amount of charging agent is about 0.1% to 5% by weight.

* * * * *